(12) United States Patent
Landis et al.

(10) Patent No.: US 12,017,000 B2
(45) Date of Patent: Jun. 25, 2024

(54) NON-SEALING HIGH FLOW THERAPY DEVICE AND RELATED METHODS

(71) Applicant: ResMed Pty Ltd, Bella Vista (AU)

(72) Inventors: Robert M Landis, Mountainside, NJ (US); Charles A Lewis, Carrabelle, FL (US); Louis Javier Collazo, Pompano Beach, FL (US); Chris Agami, Coral Springs, FL (US)

(73) Assignee: ResMed Pty Ltd (AU)

( * ) Notice: Subject to any disclaimer, the term of this patent is extended or adjusted under 35 U.S.C. 154(b) by 1046 days.

(21) Appl. No.: 15/134,735

(22) Filed: Apr. 21, 2016

(65) Prior Publication Data

US 2017/0304570 A1    Oct. 26, 2017

(51) Int. Cl.
| | |
|---|---|
| *A61M 16/16* | (2006.01) |
| *A61M 16/00* | (2006.01) |
| *A61M 16/06* | (2006.01) |
| *A61M 16/08* | (2006.01) |
| *A61M 16/10* | (2006.01) |
| *A61M 16/20* | (2006.01) |

(52) U.S. Cl.
CPC .... *A61M 16/0066* (2013.01); *A61M 16/0051* (2013.01); *A61M 16/0666* (2013.01); *A61M 16/0816* (2013.01); *A61M 16/0875* (2013.01); *A61M 16/1055* (2013.01); *A61M 16/109* (2014.02); *A61M 16/1095* (2014.02); *A61M 16/16* (2013.01); *A61M 16/203* (2014.02); *A61M 2016/0027* (2013.01); *A61M 2016/0039* (2013.01); *A61M 2016/1025* (2013.01); *A61M 16/161* (2014.02); *A61M 16/162* (2013.01); *A61M 16/209* (2014.02); *A61M 2205/3368* (2013.01); *A61M 2205/505* (2013.01); *A61M 2205/8206* (2013.01)

(58) Field of Classification Search
CPC .............. A61M 16/0066; A61M 16/16; A61M 16/109; A61M 16/0816; A61M 16/203; A61M 16/0666; A61M 16/0875; A61M 16/1095

See application file for complete search history.

(56) References Cited

U.S. PATENT DOCUMENTS

| | | | |
|---|---|---|---|
| 4,686,974 A * | 8/1987 | Sato | A61M 16/0677 128/204.23 |
| 5,226,411 A | 7/1993 | Levine | |
| 5,284,160 A | 2/1994 | Dryden | |
| 5,390,666 A * | 2/1995 | Kimm | A61M 16/024 128/204.26 |
| 5,503,146 A * | 4/1996 | Froehlich | A61M 16/024 128/202.22 |

(Continued)

OTHER PUBLICATIONS

Final Office Action mailed Dec. 14, 2020 for U.S. Appl. No. 14/016,042.

*Primary Examiner* — Timothy A Stanis
(74) *Attorney, Agent, or Firm* — Botos Churchill IP Law LLP

(57) ABSTRACT

A high flow therapy system for delivering heated and humidified respiratory gas to an airway of a patient, the system including a respiratory gas flow pathway for delivering the respiratory gas to the airway of the patient by way of a non-sealing respiratory interface; wherein flow rate of the pressurized respiratory gas is controlled by a microprocessor.

23 Claims, 14 Drawing Sheets

(56) References Cited

U.S. PATENT DOCUMENTS

| | | | | |
|---|---|---|---|---|
| 5,682,877 | A | * 11/1997 | Mondry | A61M 16/10 128/204.22 |
| 6,516,800 | B1 | 2/2003 | Bowden | |
| 6,571,794 | B1 | 6/2003 | Hansen | |
| 8,267,084 | B2 | 9/2012 | Kwok | |
| 9,205,215 | B2 | * 12/2015 | McAuley | A61M 16/06 |
| 10,449,320 | B2 | 10/2019 | Miller et al. | |
| 10,617,835 | B2 | 4/2020 | Schermeier et al. | |
| 10,737,049 | B1 | 8/2020 | Orr et al. | |
| 10,828,482 | B2 | 11/2020 | Osborne et al. | |
| 2001/0017134 | A1 | 8/2001 | Bahr | |
| 2004/0065335 | A1 | 4/2004 | Huber et al. | |
| 2006/0137445 | A1 | * 6/2006 | Smith | A61M 16/1095 73/204.22 |
| 2006/0207594 | A1 | * 9/2006 | Stenzler | A61M 16/204 128/204.18 |
| 2007/0169776 | A1 | * 7/2007 | Kepler | A61M 16/0003 128/200.23 |
| 2007/0175473 | A1 | * 8/2007 | Lewis | A61J 11/0005 128/204.18 |
| 2008/0051674 | A1 | * 2/2008 | Davenport | A61B 5/087 600/561 |
| 2008/0142019 | A1 | * 6/2008 | Lewis | A61M 16/0488 128/207.18 |
| 2013/0333701 | A1 | * 12/2013 | Herron | A61M 16/1095 128/203.27 |
| 2014/0283828 | A1 | * 9/2014 | Acker | A61M 16/0057 128/203.14 |
| 2016/0193438 | A1 | * 7/2016 | White | A61M 16/0003 128/203.12 |

\* cited by examiner

NON-SEALING HIGH FLOW THERAPY DEVICE AND RELATED METHODS

BACKGROUND

In respiratory medicine, ventilation devices are typically used to deliver respiratory gases for therapeutic effect. Ventilators have been used with invasive patient interface, such as endotracheal tubes. Bi-level, Bi-PAP, and CPAP devices have been used with non-invasive patient interfaces, such as respiratory masks. When an option, non-invasive respiratory systems are preferred for increased patient comfort and reduced risks. Non-invasive ventilation (NIV) systems such as Bi-Level PAP (positive airway pressure) require the use of a sealed patient interface, such as a full face mask. Systems with patient interface that seal on the patient (i.e. closed systems) can generate higher pressures with low flows or non-continuous flows. Sealed patient interfaces are not as comfortable or easy to apply as non-sealed patient interface, such as nasal cannulas. However, non-sealing nasal cannulas do not work properly with NIV systems. Nasal cannulas are typically used with basic oxygen delivery systems that have flow limitations for various reasons.

There is a need for a respiratory gas delivery system that works optimally with non-sealing patient interfaces to produce therapeutic effects to the patient similar to that of NIV systems. Because the system has a non-sealing patient interface and therefore some gas and pressure is lost to atmosphere, this respiratory gas delivery system must be able to deliver gas at high flows that are high enough to generate positive pressure in the patient's airway.

SUMMARY

The present disclosure relates to a high flow therapy system for delivering heated and humidified respiratory gas to an airway of a patient, the system including a respiratory gas flow pathway for delivering the respiratory gas to the airway of the patient by way of a non-sealing respiratory interface; wherein flow rate of the pressurized respiratory gas is controlled by a microprocessor.

DESCRIPTION

Figure 1:
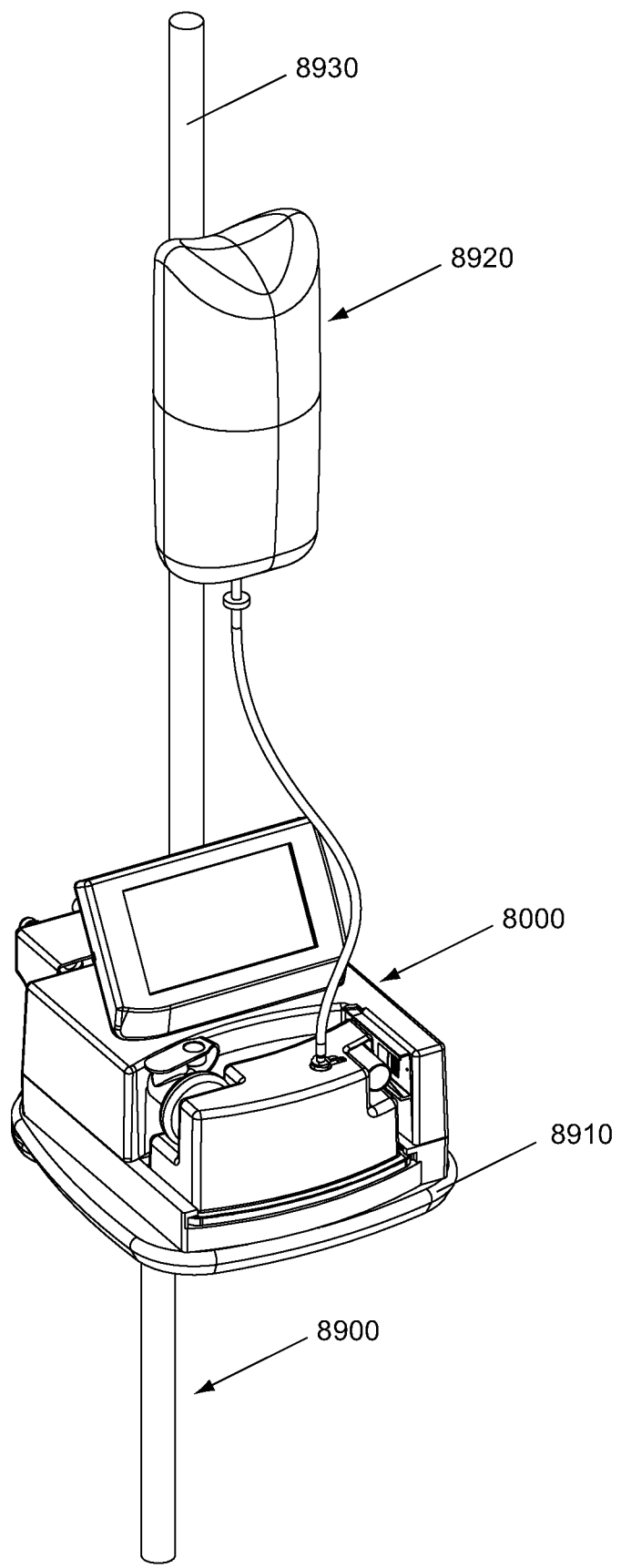
FIG. 1 illustrates a perspective view of a high flow therapy system positioned on a cart in accordance with an embodiment of the present disclosure.

The present invention is a respiratory gas delivery system that delivers high flows (i.e. high flow therapy) through a non-sealing patient interface. This High Flow Therapy (HFT) system is comprised of a HFT device (i.e. the main device) and its accessories, which are described in further detail throughout. The HFT device can provide respiratory support for patients ranging from neonates to adults. The HFT device can lower respiratory rates, improve secretion clearance, and reduce the work of breathing. The HFT device can relieve respiratory disorders that respond to certain levels of positive airway pressures, such as asthma, bronchitis, sleep apnea, snoring, COPD, and other conditions of the respiratory tract. For example, the HFT system could deliver up to 35 cm H2O of airway pressure. The HFT device can treat hypothermia and aid in washout of anesthetics after surgery. It is envisioned that the HFT device may have applications similar to those prescribed hypobaric chambers, such as brain or head injury (e.g. concussions). The present disclosure relates to a high flow therapy system for delivering heated and humidified respiratory gas to an airway of a patient. The HFT device can generate flows that are continuous. The HFT system delivers the gases to the patient via a non-sealing patient interface (e.g. nasal cannula) utilizing an "open flow" method of delivery. "Open Flow" specifies that the cannula in the patient's nose does not create a seal or near seal.

The HFT device is an all-in-one device that allows for control of gas flow, gas oxygen concentration, gas temperature, and gas humidity in a single device or system. This includes delivering gases at flow rates up to 60 L/min, oxygen concentrations up to 100%, gases heated from 30 to 40 degrees Celsius, and humidified gases up to 100% relative humidity. The is vastly superior to basic oxygen delivery systems that are limited to gas flows of up to 8 L/min, have no gas temperature control, and have no gas humidity control. Because basic oxygen delivery systems have no gas temperature or gas humidity control, gas flows higher than 8 L/min are not well tolerated by the patient. In contrast, the HFT device can deliver higher flow rates that are easily tolerated in the nasal passages when the gas is warm and humid. The high flow also assures that the patient's inspired volume may be almost entirely derived from the gas delivered (i.e. minimized or no mixture of delivered gas with ambient air). The HFT system may generate a positive pressure in the airways during inhalation and/or exhalation, even though the system is an open system (i.e. does not use a sealing patient interface).

An all-in-one HFT device allows for more control and more accuracy of the gas conditions being delivered. It also provides the opportunity to provide feedback to the operator and to provide feedback loop control of the HFT device through for example gas sensing. Finally, an all-in-one HFT device allows for improved communications and alarms to the operator. For example, the HFT device may gather airway pressure information through its pressure sensing technology described throughout and use that information to adjust flow rates (either manually by the operator or automatically by the HFT device) in order to control airway pressures (e.g. prevent unintended high pressures).

Figure 2:
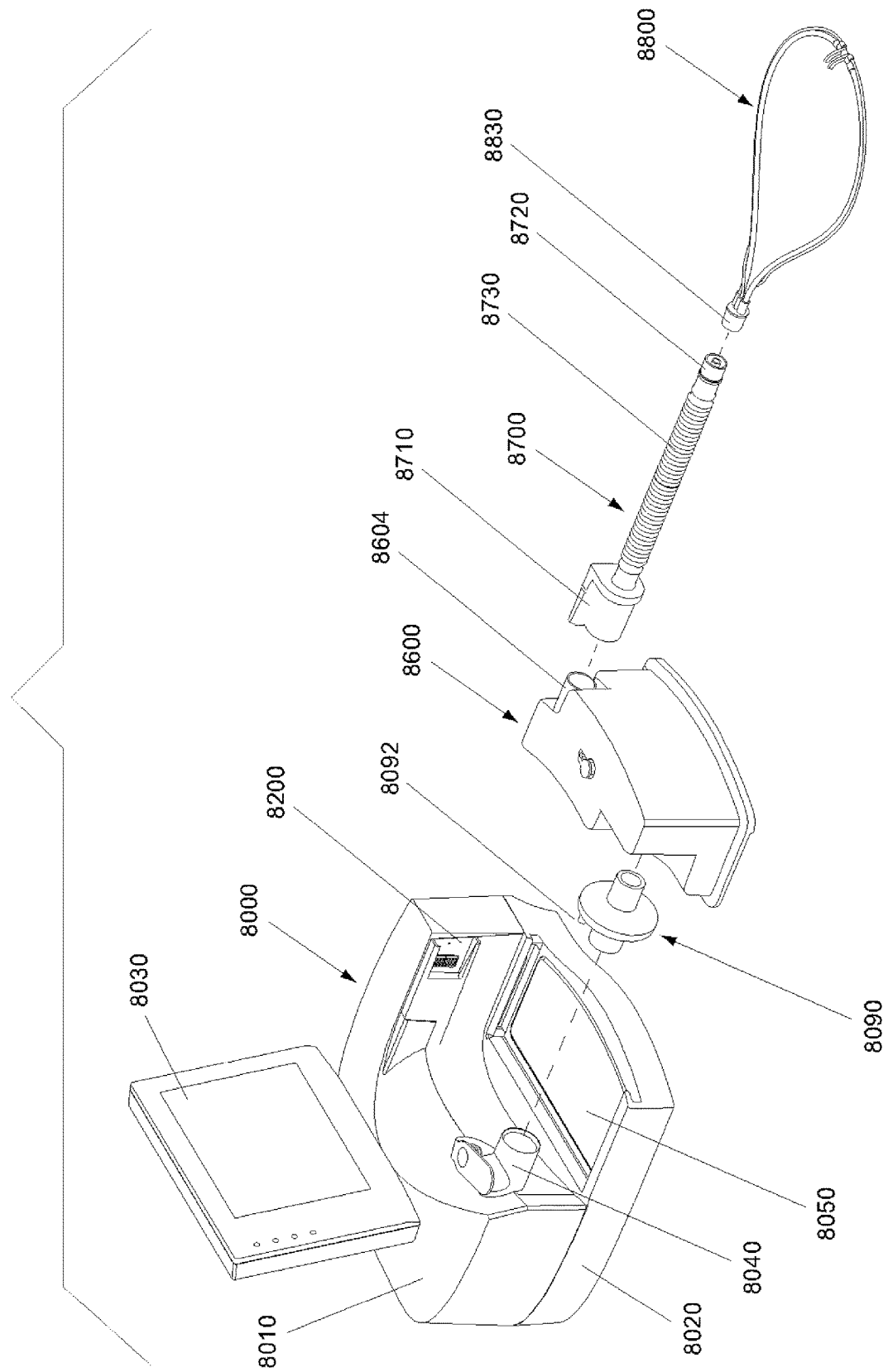
FIG. 2 illustrates an exploded view of the high flow therapy system of FIG. 1 illustrating the major components in a disassembled relationship, in accordance with an embodiment of the present disclosure.
Figure 3:
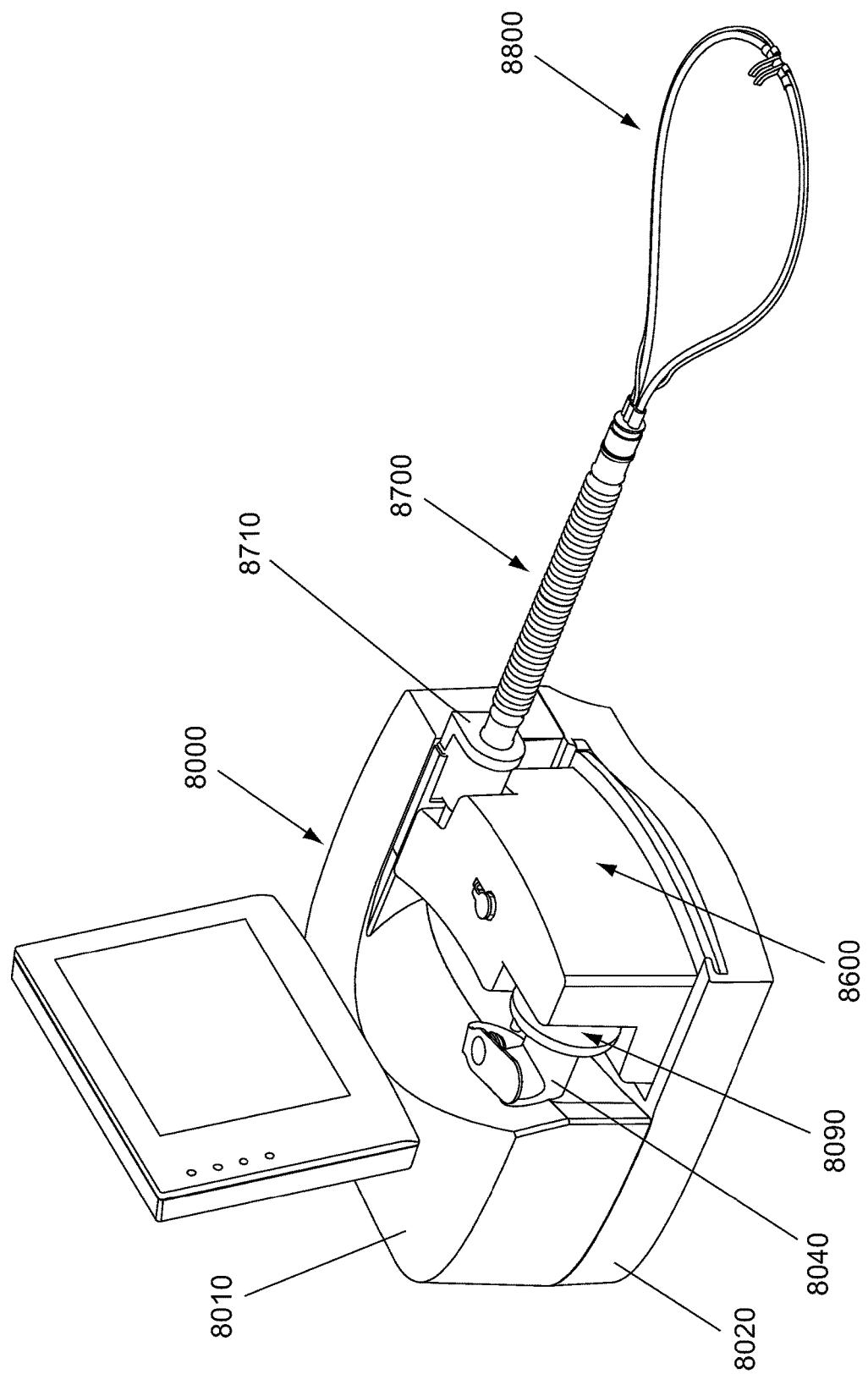
FIG. 3 illustrates an assembled view of the high flow therapy system of FIG. 1 illustrating the major components in an assembled relationship, in accordance with an embodiment of the present disclosure.
Figure 4:
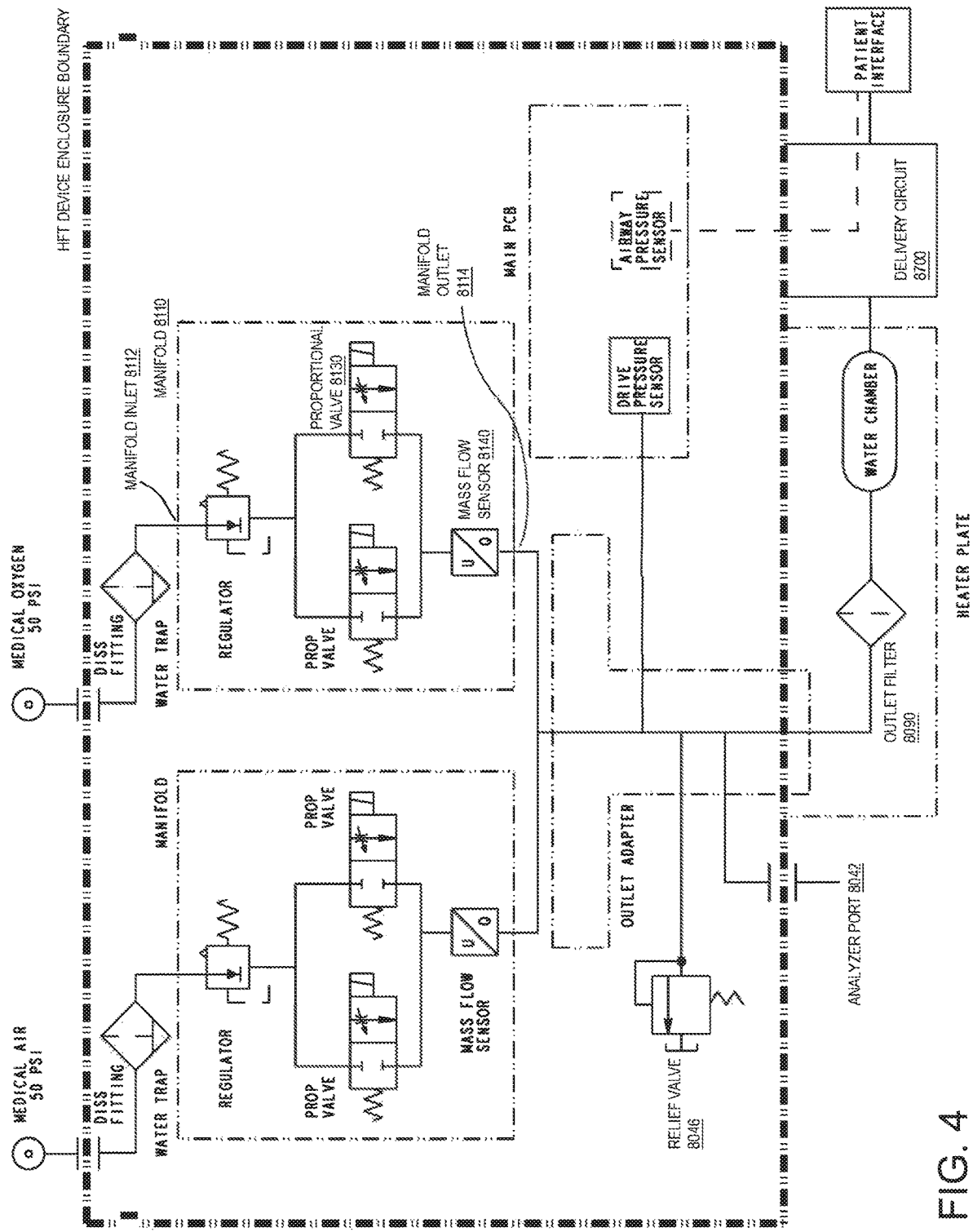
FIG. 4 illustrates a schematic view of the high flow therapy system of FIG. 1 in accordance with an embodiment of the present disclosure.

The HFT system is a microprocessor-controlled respiratory gas delivery system that provides continuous flows of heated and/or humidified air and/or oxygen mixtures to patients. FIG. 1 illustrates of an embodiment of a HFT device 8000 of a HFT system that is positioned on a platform of a cart 8900 and coupled with a water bag 8920. FIG. 2 illustrates an exploded view of some of the main components of an HFT system, including the HFT device 8000, the water chamber 8600, the delivery circuit 8700, and the patient interface 8800. FIG. 3 illustrates an assembled view of some of the main components of an HFT system. FIG. 4 illustrates a schematic view of some of the main components of an HFT system. The HFT device 8000 can be controlled by a microprocessor on a main PCB (printed circuit board) 8060. The operator of the HFT device inputs settings, such as gas flow rate, gas temperature, gas oxygen concentration, gas humidity levels, etc. via the HFT device's user interface for the microprocessor to control. The user interface may be a graphical user interface (GUI). The user interface may contain information such as graphs (e.g. pressure waveform), numbers, alpha characters, help menus, etc. The user interface may be shown on a display 8030. The display 8030 can have a touch screen that allows the operator make inputs to the HFT device. The display 8030 can be rotated, for example up to 360 degrees, to facilitate viewing or entry. The display 8030 can be pivoted or tilted, for example from 0 to 180 degrees, to facilitate viewing, entry, or shipping. The display 8030 can be removable to facilitate shipping, servicing, or to be used as a portable user interface. The HFT device can also include push buttons or knobs as part of the user interface system. In alternative embodiments, the information on the display 8030 may be projected by the HFT device (e.g. on a wall or on a table) or the information may be transmitted onto another device, such as a hand held device or computer. In another alternative embodiment a separate device, such as phone, tablet, or computer may couple with the HFT device in lieu of the display 8030 or may transmit information to the HFT device in order to serve as the user interface.

Figure 5:
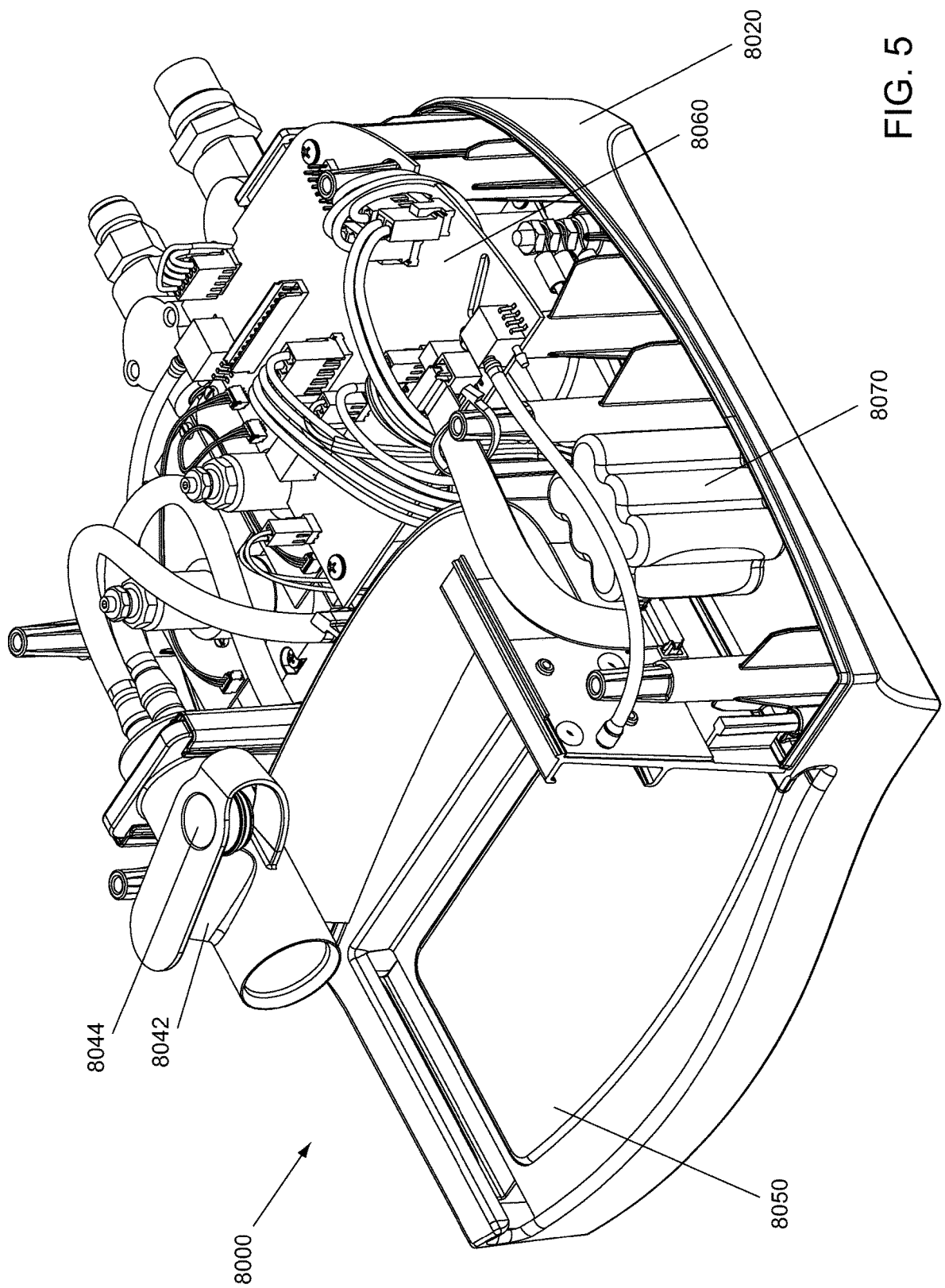
FIG. 5 illustrates a top perspective view of the high flow therapy device of FIG. 1 showing internal components with the upper enclosure removed, in accordance with an embodiment of the present disclosure.
Figure 6:
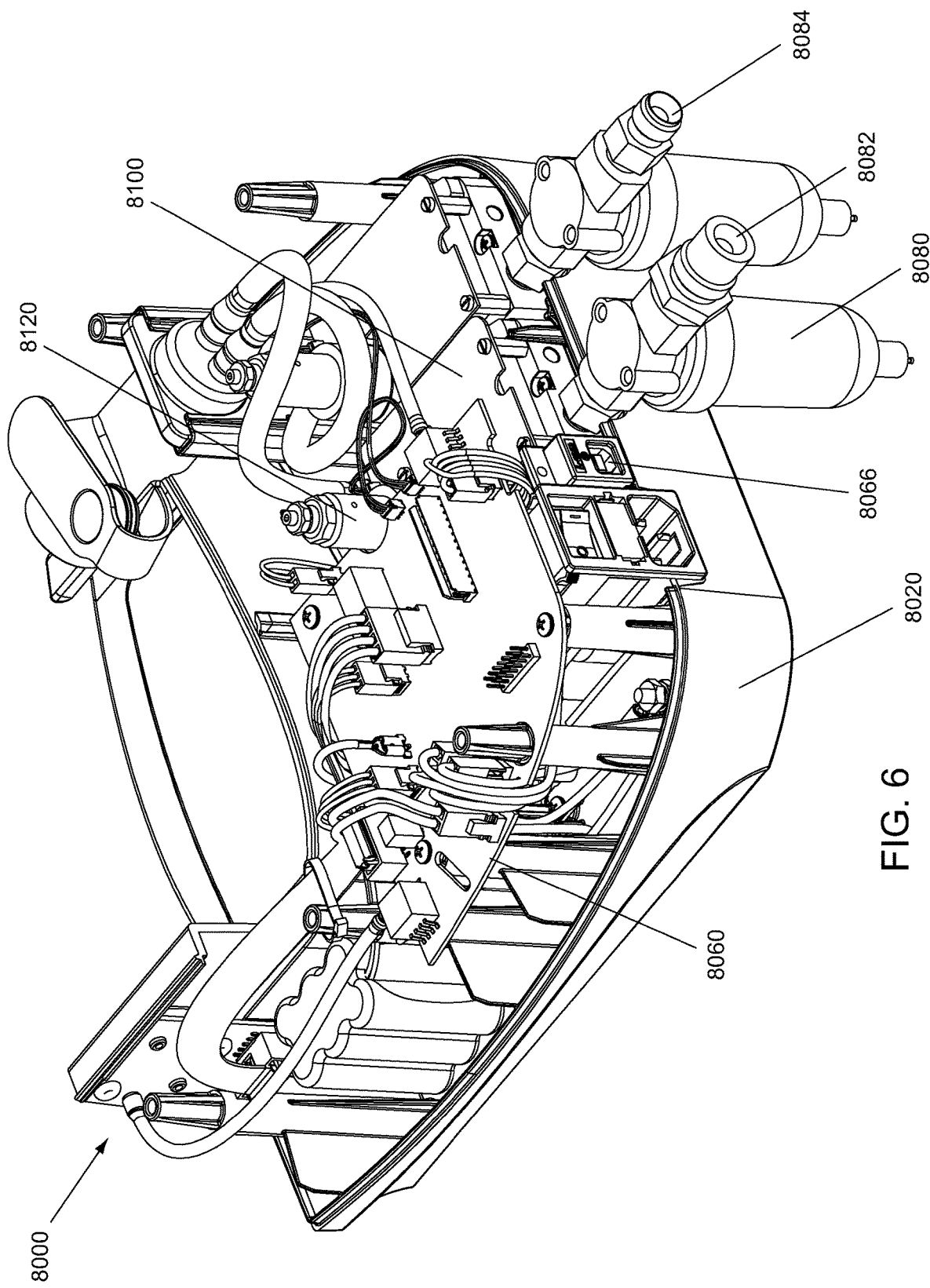
FIG. 6 illustrates a rear perspective view of the high flow therapy device of FIG. 1 showing internal components with the upper enclosure removed, in accordance with an embodiment of the present disclosure.
Figure 7:
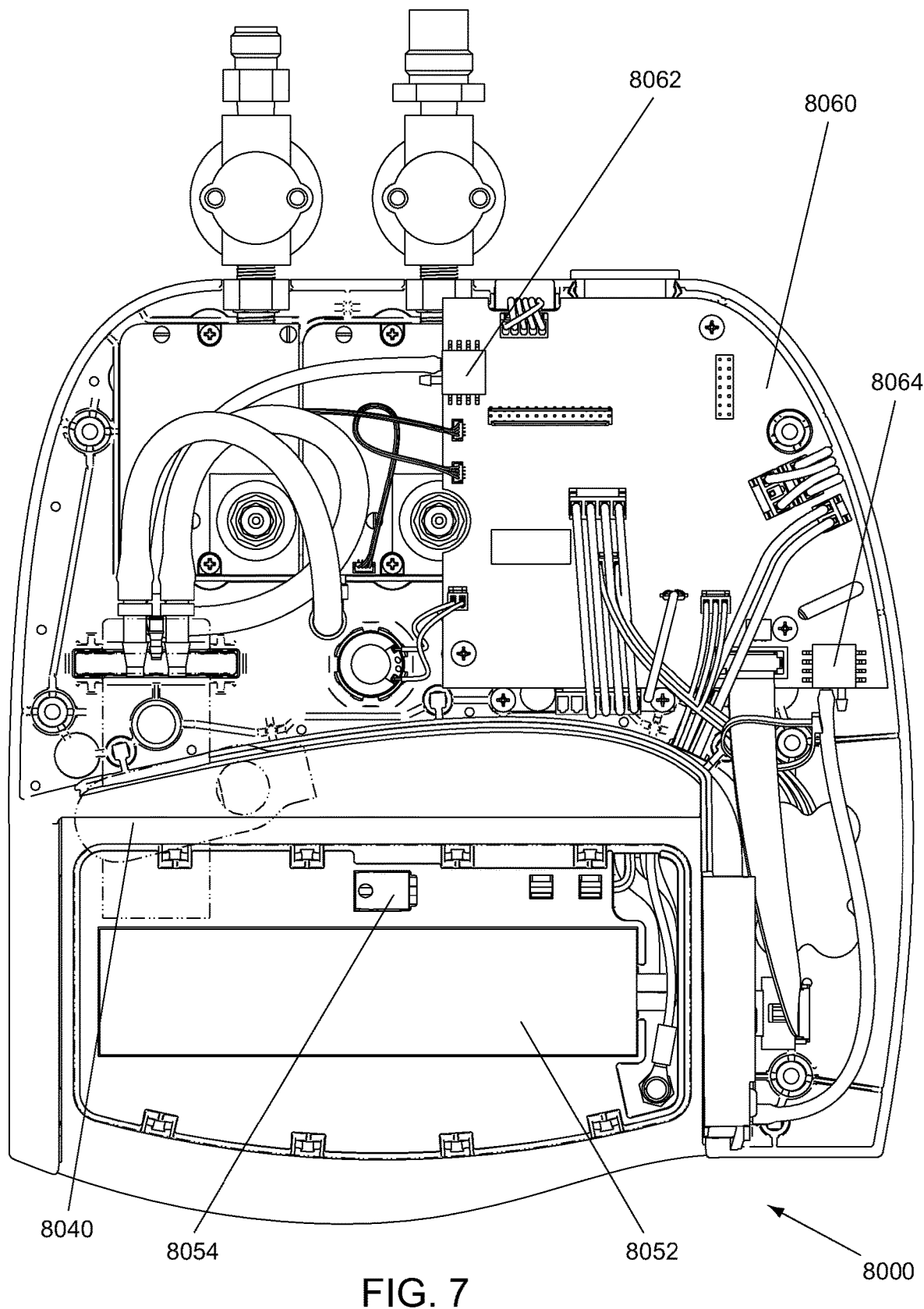
FIG. 7 illustrates a top view of the high flow therapy device of FIG. 1 showing internal components with the upper enclosure removed, the heater plate shown transparent, and the outlet adapter shown transparent, in accordance with an embodiment of the present disclosure.

The HFT device 8000 may have an enclosure with an upper enclosure portion 8010 and a lower enclosure portion 8020 as shown in FIG. 2. FIG. 5 illustrates a top perspective view of the HFT device 8000 with the upper enclosure portion 8010 removed to show some of the internal components. FIG. 6 illustrates a rear perspective view of the HFT device 8000 with the upper enclosure portion 8010 removed to show some of the internal components. FIG. 7 illustrates a top view of the HFT device 8000 with the upper enclosure portion 8010 removed, the heater plate 8050 shown transparent, and the outlet adapter 8040 shown transparent to show some of the internal components. The HFT device 8000 may have a battery 8070 so that it may work, at least partially, as a portable device, without being plugged in, or without wall power (e.g. as a backup battery in a power outage). The HFT device may be mounted on a pole 8930, on a cart 8900, or may be configured to be placed on a table, desk, or nightstand.

Medical grade air and/or medical grade oxygen, for example from hospital gas supply systems or compressed gas tanks, may be used with the HFT system. Other gases, such as helium, may be substituted for the air or oxygen. An inlet filter 8080 (e.g. a water trap) can be connected between a gas source and the HFT device 8000 via a fitting 8082 (e.g. DISS fitting). The inlet filter 8080 could be internal or conversely external to the HFT device so it is visible and accessible for service. The pressurized gas (e.g. air or oxygen from the facility at 50 psi) then enters the HFT device 8000 and its flow system. There may be two inlet filters as shown in FIG. 6. There may be two different fittings (e.g. fitting 8082 and second fitting 8084) for connecting the HFT device 8000 with different gas sources.

The HFT device can have an integrated flow adjustment system to deliver the set flow rate and/or oxygen concentrations to the patient. Flow control can be achieved automatically through the interaction between the system electronics (e.g. the microprocessor) and the flow system. The flow system can consist of valve systems. Valve system scan be used for air and/or oxygen gas flow regulating and metering. The valve systems can be partially or completely enclosed in the HFT device.

A valve system 8100 can be a manifold 8110 (e.g. a molded housing or machined block of plastic or aluminum). A manifold 8110 can have one manifold inlet 8112, one manifold outlet 8114, and one manifold flow path there between. In an alternate embodiment, a single manifold can have a first manifold inlet, a first manifold outlet, and a first manifold flow path there between, as well as a second manifold inlet, a second manifold outlet, and a second manifold flow path there between. In a preferred embodiment, there are two valve systems inside the unit—one for air and one for oxygen. A regulator 8120 can be mounted on the manifold 8110. The regulator 8120 can reduce the gas pressure from its initial pressure (e.g. 50 psi) to a lower or constant pressure that is optimal for subsequent flow rate control inside the device. The pressurized gas flows from the manifold inlet 8112 to the regulator 8120 that is mounted on the manifold 8110. After leaving the regulator 8120, the gas flows through a proportional valve 8130 that can also be mounted on the manifold 8110. The proportional valve 8130 can be a piezo-actuated proportional valve. The proportional valve 8130 can output a gas flow rate proportional to a signal voltage. The proportional valve 8130 is normally closed when no gas flow is required through the valve. In a preferred embodiment, each valve system can have two proportional valves, where a first proportional valve accommodates higher flow rates (e.g. 50 L/min) and a second proportional valve accommodates lower flow rates (e.g. 1 L/min). In this embodiment, the two proportional valves may work independently or may work in cooperation.

The valve system 8100 can have a mass flow sensor 8140 coupled with the manifold 8110 to measure the flow rate of the gas. The mass flow sensor 8140 is coupled to a manifold PCB (printed circuit board), which can be mounted to the manifold 8110. The manifold PCB is electrically connected to the main PCB 8060 to communicate input/output signals and power. This system can be referred to as a 2-position (i.e. on and off), 2-way (i.e. gas in and gas out) piezo-based valve system with integral mass flow metering system. This system can be described as a low-power, highly-sensitive piezo valve working in conjunction with a mass flow sensor and with control loop electronics to achieve accurate flow rates with little power consumption. The results are that the valve systems can be very quiet and cool, eliminating the needs for fans or secondary cooling devices (e.g. heat sinks) inside the HFT device. This integrated flow adjustment system described in the sections above forms a control loop by which the gas flow may be adjusted by the software of the HFT device.

Gas exists the manifold 8110 through the manifold outlet 8114. In an embodiment with two manifolds (i.e. one for each gas), the gases exit their respective manifolds and stream together to mix. This mixing can occur in a tube, a mixing chamber, a blender, etc. In an embodiment with one manifold for two different gases, the gases may stream together within the manifold to mix prior to exiting the manifold (i.e. two manifold inlets and one manifold outlet).

In another embodiments, the HFT device can entrain air from ambient instead of receiving it from a compressed gas source. In yet another embodiment, the HFT device can have an integral blower for air to advance the gas. Both of these embodiments could replace the air valve system and integrate with the flow adjustment system. Gas from these embodiments could still mix with the oxygen downstream as previously described.

Mixed gases can then proceed towards and through an outlet adapter 8040. Pressure inside the outlet adapter 8040 can be measured by a drive pressure sensor 8062. The drive pressure sensor 8062 can be located on the main PCB 8060 and can be pneumatically connected to the bore of the outlet adapter 8040 by a length of flexible tubing. If the pressure inside the outlet adapter 8040 exceeds a certain pressure (e.g. 1 psi), the gas may be vented out of the outlet adapter 8040 through a relief valve 8046.

The end of the outlet adapter 8040 may protrude outside the HFT device 8000 enclosure. The outlet adapter 8040 can feature an oxygen analyzer port 8042 into which an oxygen analyzer may be connected to for oxygen concentration (e.g. FiO2) verification purposes. The oxygen analyzer port 8042 may be closed by a valve, plug, or cap when an analyzer is not in use. Such a feature may be coupled or integral with the outlet adapter 8040 to close off the oxygen analyzer port 8042. An analyzer adapter may be inserted into the oxygen analyzer port 8042 to allow the fit of different sizes of oxygen analyzers. In one embodiment, an analyzer adapter 8044 may be integrated into the outlet adapter.

An outlet filter 8090 may be connected to the outlet adapter 8040 (e.g. via press fit). This outlet filter may have viral and/or anti-bacterial properties. The outlet filter 8090 serves to keep bacteria, viruses, volatile organic compounds, etc. from entering the water chamber and eventually reaching the patient. The outlet filter 8090 also serves to keep water, humidity, bacteria, viruses, etc. from entering the HFT device itself. This keeps undesirable matter from collecting inside the HFT device and potentially being transmitted to the next patient that uses the HFT device. The outlet filter 8090 therefore is a safety component to reduce risks to the HFT device and the patient from use of the HFT device. The outlet filter 8090 may have a outlet filter gas sampling port 8092. The outlet filter 8090 may have a straight, angled, or staggered filter body portion, filter inlet gas port, and/or filter outlet gas port. The end of the outlet adapter 8040 may be closed by a valve, plug, or cap when the outlet filter 8090 is not engaged, for example between use of the HFT device on different patients. Such a feature may be coupled or integral with the outlet adapter 8040 and would serve to protect the inside of the HFT device when an outlet adapter 8040 is not present.

The outlet filter and the other components downstream may be considered single use, single patient use, or disposable components. These components may include a water chamber, a delivery circuit, a patient interface (e.g. cannula; mask; or artificial airways such as endotracheal tubes, nasotracheal tubes, and tracheotomy tubes), a tee, and/or other fittings. It is preferred that the patient interface be a non-sealing interface (i.e. not intended to form a substantial seal with the patient), such as a non-sealing nasal cannula.

The water chamber 8600 slides into the HFT device 8000 and subsequently engages with outlet filter 8090 (via a friction fit). The HFT device 8000 has receiving flanges that couple with the water chamber 8600. The receiving flanges can be spring loaded to facilitate securing the water chamber 8600 and/or to facilitate keeping contact between the heat transfer plate of the water chamber 8600 and the heater plate 8050. The water chamber 8600 can maintain in the HFT device via an upward force and/or friction between the water chamber 8600 and the HFT device 8000. The water chamber 8600 can be inserted or removed without having to manipulate (e.g. press down) another feature, such as latch or bar.

The water chamber 8600 has a water chamber gas inlet and a water chamber gas outlet 8604. The water chamber gas inlet can have a water chamber gas inlet axis and the water chamber gas outlet 8604 can have a water chamber gas outlet axis. The water chamber gas inlet axis and the water chamber gas outlet axis may be parallel. Further, a plane drawn between the water chamber gas inlet axis and the water chamber gas outlet axis may be parallel to a typical table, nightstand, or desk located in the use environment, a platform 8910 on a cart 8900 or I.V. pole (e.g. pole 8930) where the HFT device may be placed during use, or the bottom of the HFT device itself. The gas moves through the water chamber 8600 picking up heat and/or humidity and then into the delivery circuit 8700. It is preferred that the humidified gas that exits either the water chamber 8600 not enter into or through a portion of the HFT device itself to avoid risk of contamination or the need to clean or disinfect that portion of the HFT device prior to use on another patient.

The water chamber 8600 can consist of a housing that is clear (e.g. made of a resin such as polystyrene) that allows the operator to see the water level inside. The water chamber 8600 can have a heat transfer plate (e.g. made of metal such as aluminum). The heat transfer plate may be bonded to the housing (e.g. UV cured adhesive). In an alternate embodiment, a gasket (e.g. an o-ring) may be used to couple and/or seal the heat transfer base plate to the housing. The water chamber 8600 may have an inlet baffle on the water chamber gas inlet to prevent water from splashing towards the outlet filter 8090. The water chamber 8600 may have an outlet baffle on the water chamber gas outlet 8604 to prevent water from splashing towards the delivery circuit 8700, for example during movement or transportation of the HFT device.

The operator may fill the water chamber 8600 manually with water up to a maximum level, which may be indicated by markings on the water chamber 8600. In a preferred embodiment, the water chamber 8600 may have an automatic filling system to replace the otherwise manual process of filling the water chamber 8600 with water from a sterile water bag (e.g., water bag 8920) that is suspended above the HFT system. In a manual arrangement, the operator must attend to the device periodically, as needed, in order to verify that the water chamber 8600 is being kept at a water level that is adequate for the device to function normally. If the water level is too low, water must be added to the water chamber 8600. The manual filling process usually involves the operator physically releasing a pinch valve (or other valve mechanism) that normally impedes water flow from the sterile water bag's tubing and waiting a few moments for the water chamber 8600 to fill to the correct level before re-closing the valve. Maintaining a water level that is adequate for normal device function is necessary to prevent unwanted interruptions to therapy. If the water chamber 8600 is allowed to reach a very low level or empty water level, the device may signal an audible alert. If the low water condition is not addressed in time, the device may either continue to supply under-humidified respiratory gas or may automatically pause the gas delivery until the condition is resolved. The advantages of an automatic filling system is that it ensures an adequate water level (e.g. a continuous level, such as a predetermined minimum level) in the water chamber 8600 until the water bag 8920 is empty and that it eliminates the need for operator involvement in the interim. With the automatic filling system, when the water is released into the water chamber 8600 from the water bag 8920, the water level inside the water chamber 8600 will rise until a plastic float component inside seals the fill port. As the water is consumed by the heated humidification process, the water level falls and the float lowers, allowing more water from the water bag 8920 to fill the water chamber 8600 again until the port is re-sealed. If left unattended, this process will continue until the water bag 8920 is completely empty.

The delivery circuit 8700 provides a conduit for the heated and/or humidified respiratory gas as the gas is transported from the water chamber 8600 to the patient interface. The delivery circuit 8700 may have a heating element inside, such as a heated wire 8740. The heated wire 8740 may extend through some or all of the delivery circuit. The heated wire 8740 may be straight, coiled like a spring, or embedded in the delivery circuit 8700. The delivery circuit 8700 actively maintains the desired humidity and temperature parameters of the gas and prevents and/or minimizes rainout or excessive moisture condensation inside the delivery circuit 8700. Rainout is a concern for the safety of the patient.

Figure 8:
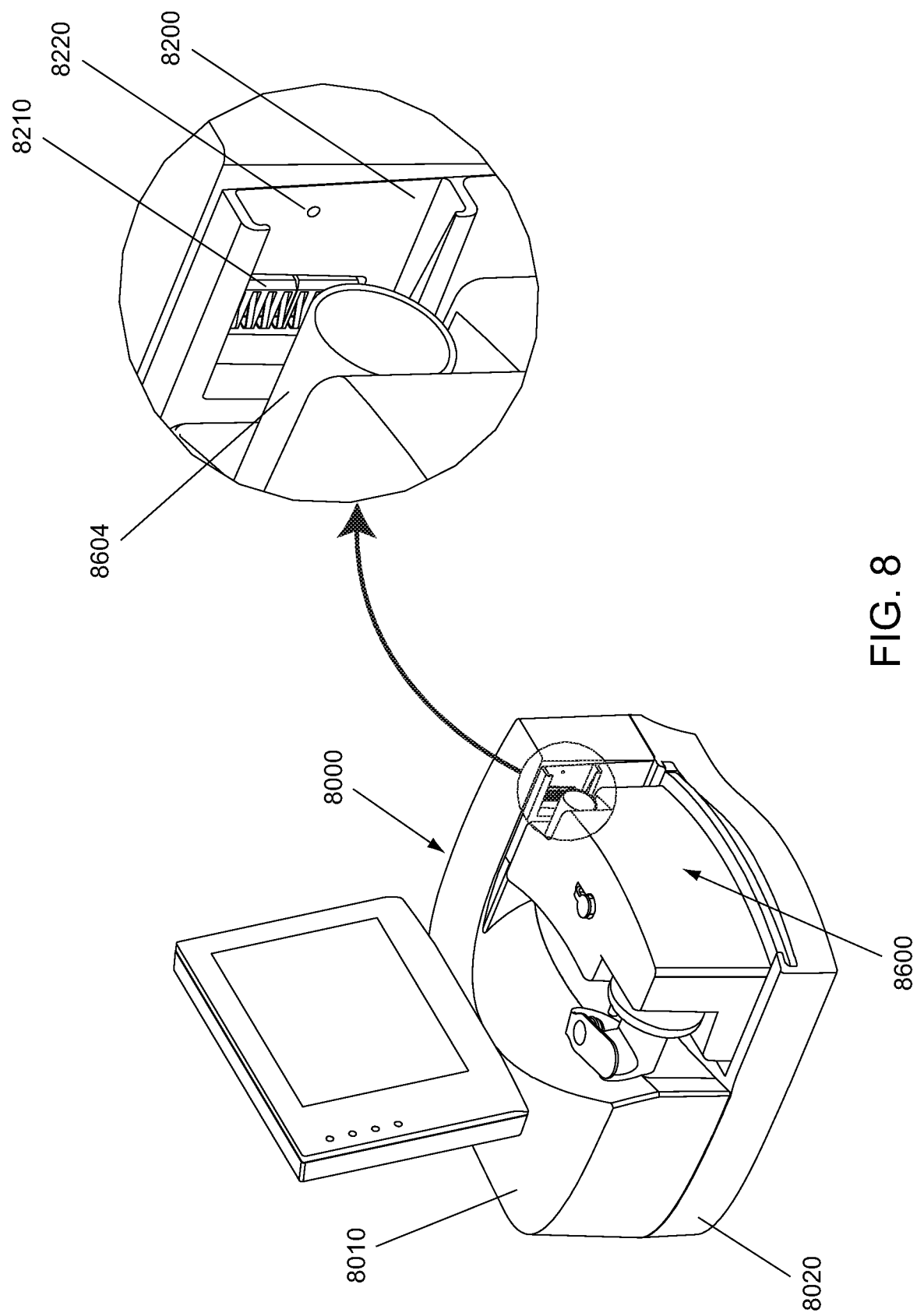
FIG. 8 illustrates a receiving area for a first connector of a delivery circuit according to an embodiment of the present disclosure.
Figure 9:
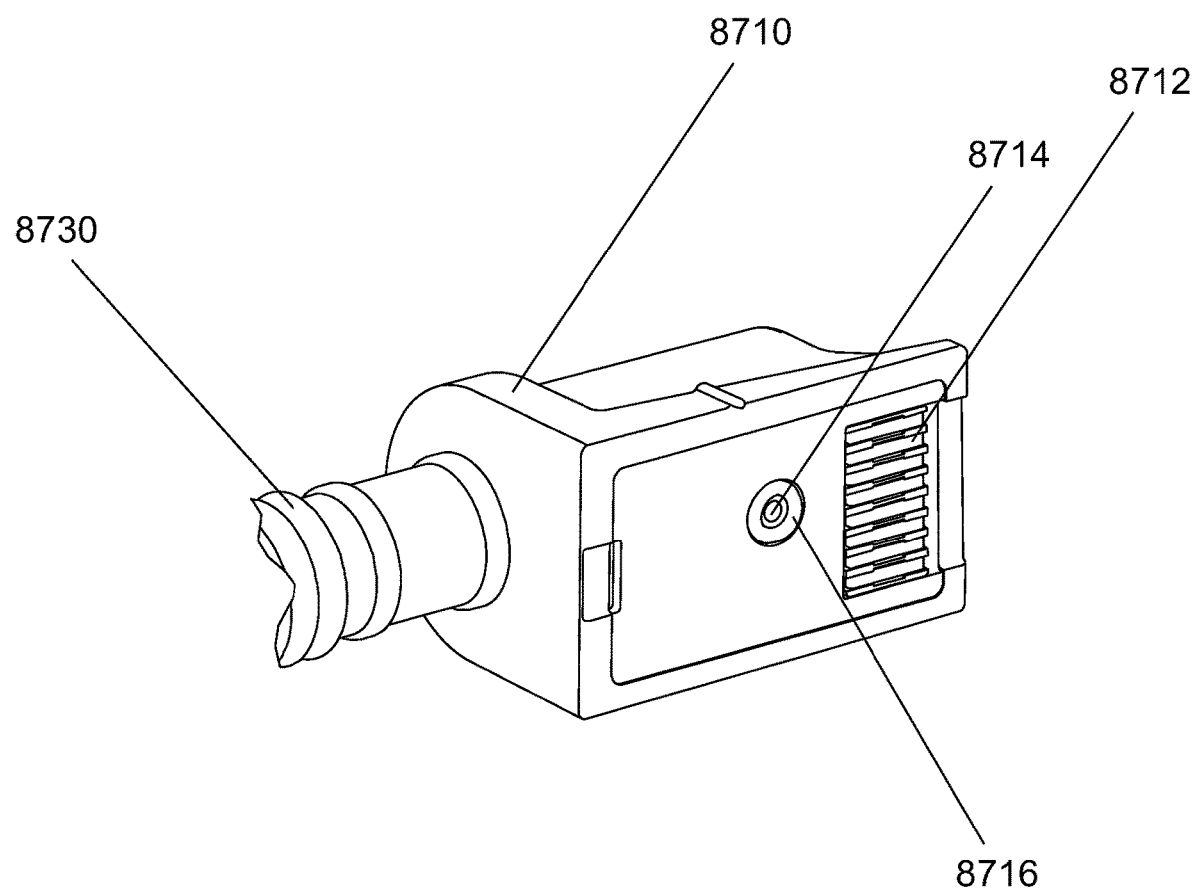
FIG. 9 illustrates the first connector of the delivery circuit according to an embodiment of the present disclosure.
Figure 10:
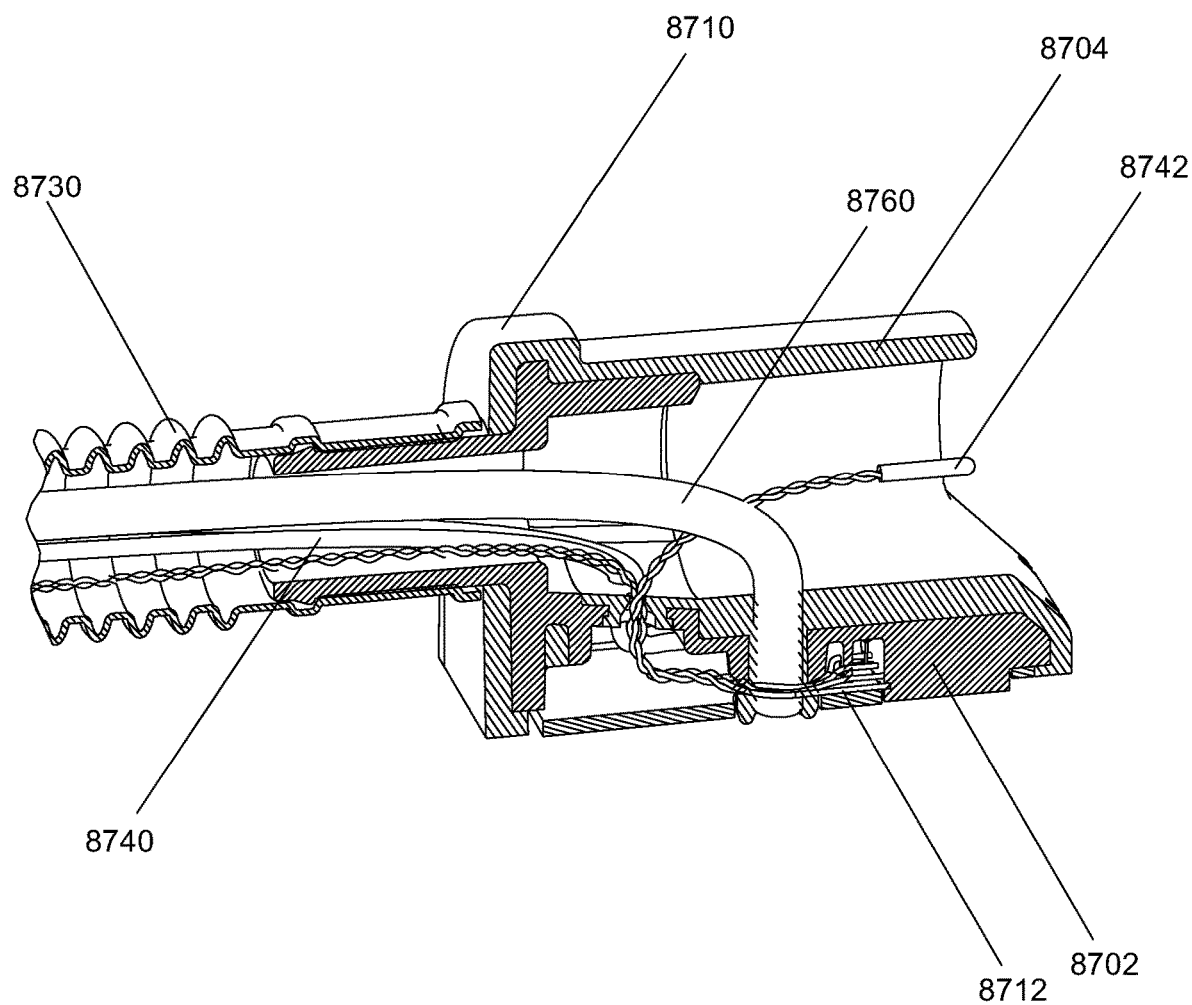
FIG. 10 illustrates a perspective sectional view of the first connector end of the delivery circuit according to an embodiment of the present disclosure.

The delivery circuit 8700 can have a first connector 8710, a second connector 8720, and a tube 8730 (e.g. a corrugated tube) there between. The first connector 8710 can connect the delivery circuit 8700 to the water chamber 8600. FIG. 10 illustrates a perspective sectional view of an embodiment of first connector end and the tube 8730 of the delivery circuit 8700. The first connector 8710 may have a body that is rigid (e.g. rigid portion 8702) and provides structure, such as a plastic, and that houses first connector electrical contacts 8712. The first connector electrical contacts 8712 may be integrally molded into the body. Alternatively, the body may be flexible, have a flexible portion (e.g. by overmolding), or have a flexible portion (e.g. flexible portion 8704) that is coupled with the rigid portion 8702. The first connector 8710 (or its flexible portion) can facilitate sealing and/or coupling the first connector 8710 with the water chamber 8600 (e.g., at water chamber gas outlet 8604). The first connector (or its flexible portion) can facilitate coupling the delivery circuit 8700 to the enclosure of the HFT device. For example, the first connector 8710 (or its flexible portion) conforms to a mating socket 8200 in the enclosure of the HFT device 8000 to provide a snug, secure mechanical engagement. FIG. 8 illustrates mating socket 8200, contacts 8210, and sensor port 8220 of HFT device 8000, as well as water chamber gas outlet 8604 of water chamber 8600. FIG. 9 illustrates first connector 8710, first connector contacts 8712, first connector sensor port 8714, and first connector o-ring of delivery circuit 8700. The delivery circuit 8700 may couple with the HFT device 8000 or the water chamber 8600 via a friction fit. The first connector 8710 (through either the rigid portion or the flexible portion) can provide a hand-grip for the user to insert or remove the delivery circuit 8700 from the water chamber 8600 and/or the HFT device 8000.

The delivery circuit 8700 can also have a long, flexible sensing conduit (e.g., sensing conduit 8760) (and/or or a sampling conduit in other embodiments) that is internal to the delivery circuit (i.e. routed through the annular flow path through the tube 8730). In an alternate embodiment, the sensing conduit 8760 may be external (but possibly coupled) to the delivery circuit 8700. In another alternate embodiment, the tube 8730 could be a multiple lumen tube where a first lumen is the gas delivery path, a second lumen is the sensing conduit (or a sampling conduit), and possibly a third lumen is a sampling conduit. The sensing conduit 8760 (via a first connector sensor port 8714) can pneumatically connect the HFT device (via a sensor port 8220 on its enclosure) to the distal end of the patient interface (e.g. distal end of second conduit 8820). The use of a sensing conduit (or sampling conduit) can allow all electrical sensing components required for signal processing to remain inside the HFT device with the other electronics, rather than having electrical sensing components in one of the disposable components (e.g. on the distal end of the patient interface).

When the delivery circuit 8700 is coupled with the HFT device 8000, a seal can be created between the sensor port 8220 on the HFT device and the first connector sensor port 8714 in the delivery circuit 8700. The delivery circuit or the HFT device may have a seal (e.g. first connector o-ring 8716) to facilitate this seal. When the delivery circuit is coupled with the enclosure of HFT device, the first connector contacts 8712 on the delivery circuit can engage with contacts 8210 on the HFT device 8000. This electrical engagement can enable the control of the thermal components in the delivery circuit 8700 by the software of the HFT device to maintain the desired temperature and humidity parameters of the gas. The delivery circuit 8700 may also have at least two temperature sensors (e.g. thermistors) internally. A first thermistor 8742 can be located near the first connector 8710 and a second thermistor 8744 can be located near the second connector 8720. The thermistors can provide temperature feedback to the main PCB 8060 via the electrical contact engagement between the delivery circuit 8700 and the HFT device. The heated wire 8740 is powered by the HFT device via the electrical contact engagement between the delivery circuit 8700 and the HFT device.

Figure 11:
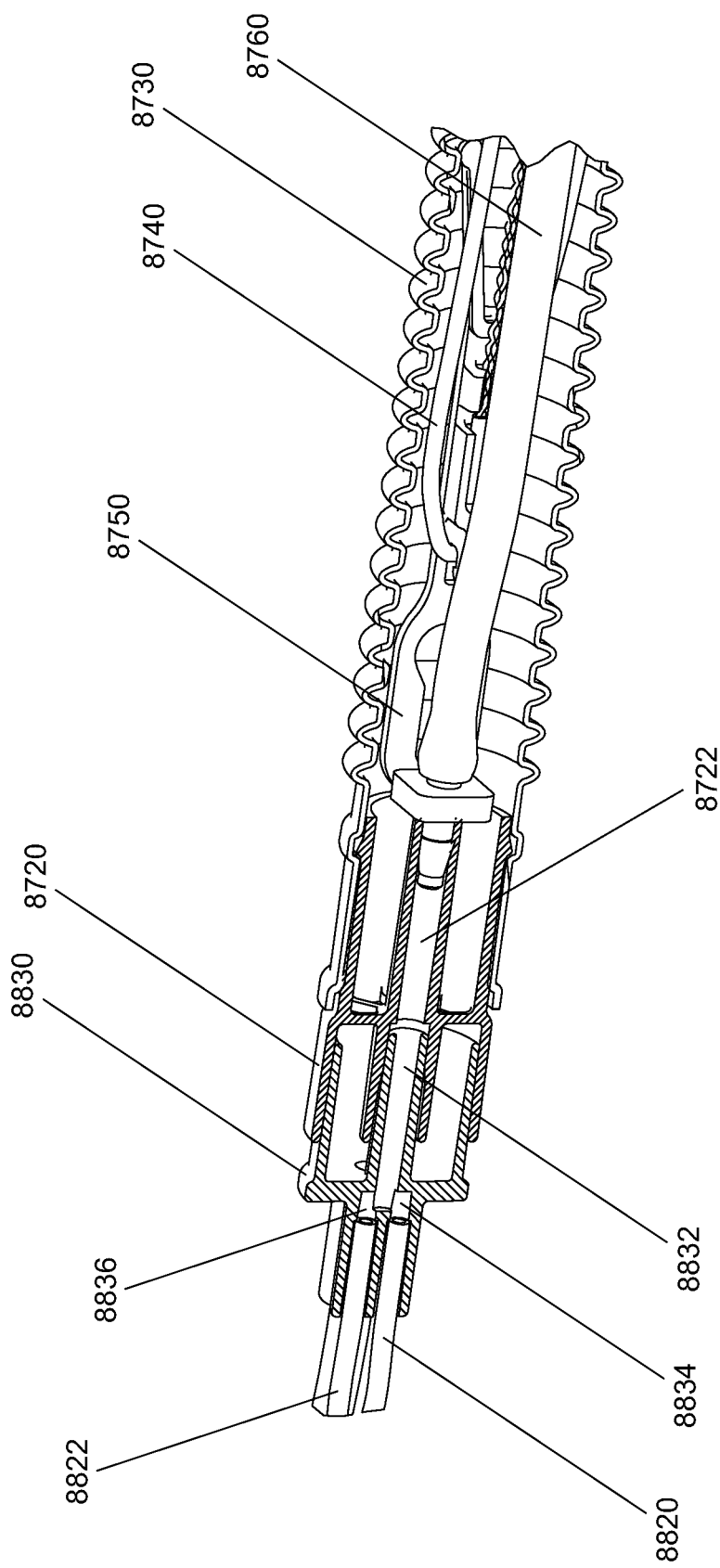
FIG. 11 illustrates a first perspective sectional view of a second connector the delivery circuit and patient fitting of the patient interface according to an embodiment of the present disclosure.
Figure 12:
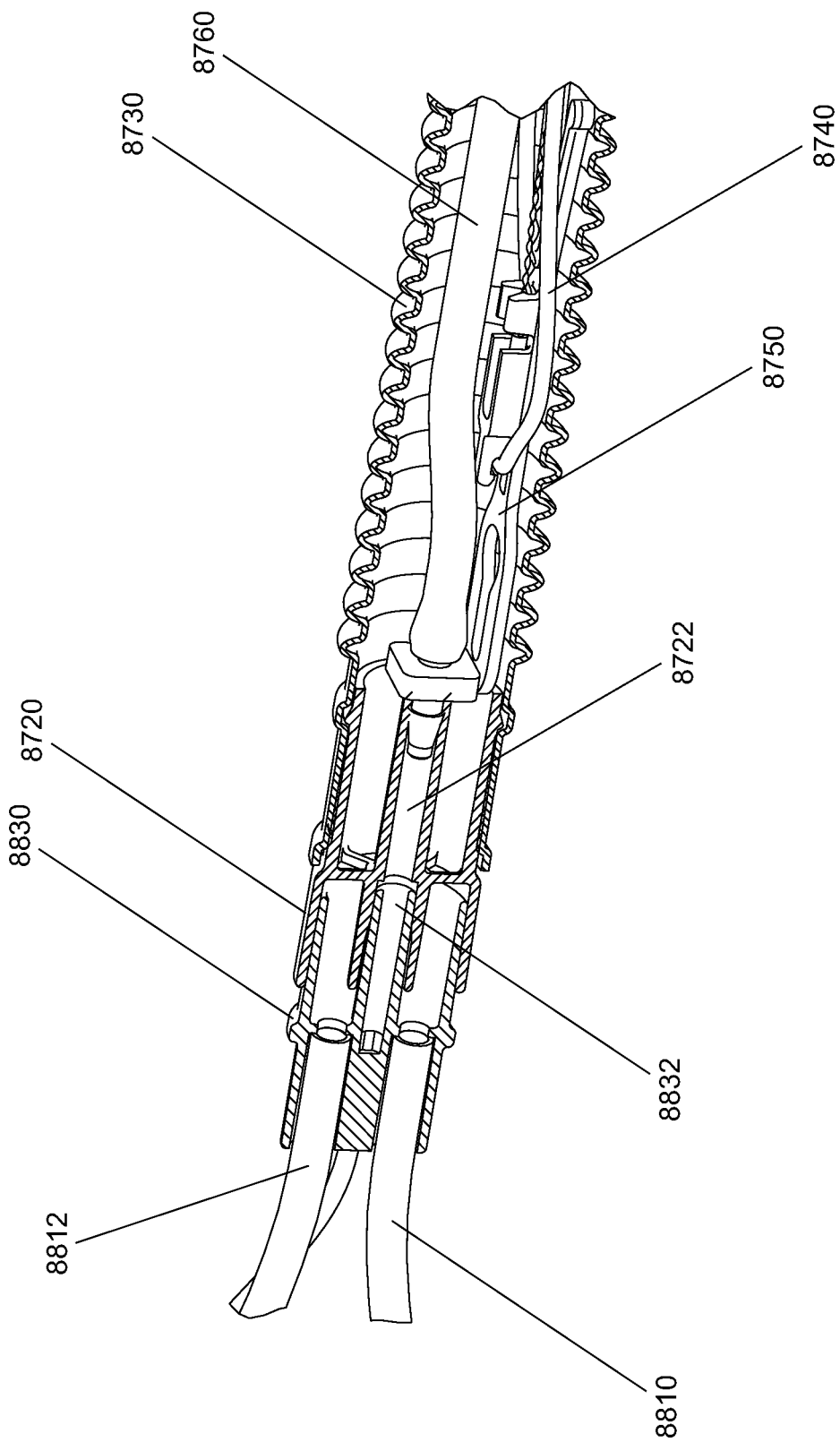
FIG. 12 illustrates a second perspective sectional view of a second connector the delivery circuit and patient fitting of the patient interface according to an embodiment of the present disclosure.
Figure 13:
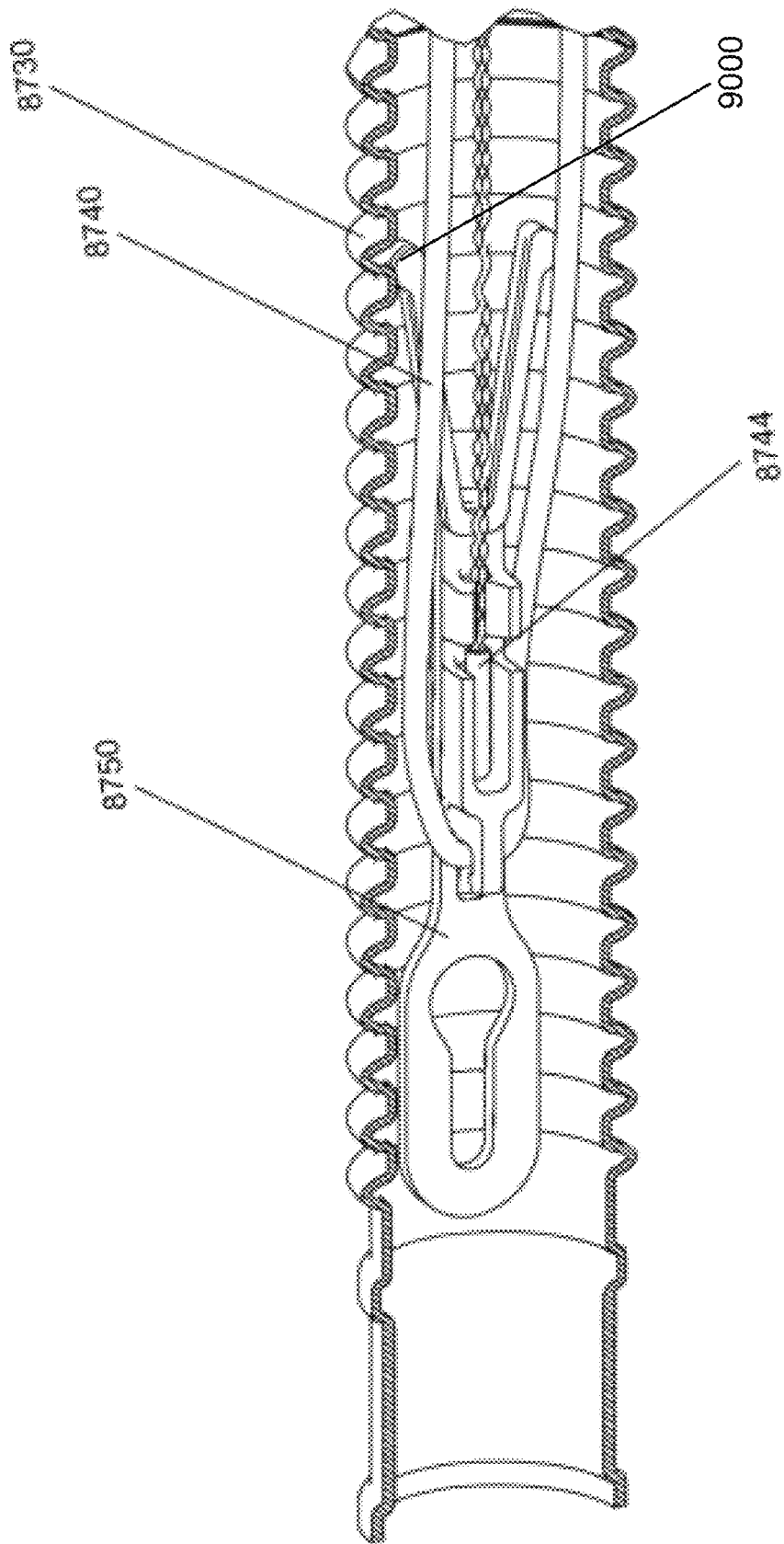
FIG. 13 illustrates a perspective sectional view of the delivery circuit at the second connector end with the second connector and sensing conduit removed, according to an embodiment of the present disclosure.

FIG. 11 illustrates a first perspective sectional view of an embodiment of the second connector end of the delivery circuit 8700 and the patient fitting end of the patient interface. FIG. 12 illustrates a second perspective sectional view of an embodiment of a second connector end of the delivery circuit 8700 and a patient fitting end of the patient interface. FIG. 13 illustrates a perspective sectional view of an embodiment of the second connector end of the delivery circuit 8700 with the second connector and the sensing conduit removed to show some of the internal components.

The delivery circuit 8700 can have a holder 8750 internal and near the second connector 8720. The holder 8750 can couple with the second thermistor 8744 and/or the heated wire 8740. The holder 8750 can provide a means for pulling during assembly the second thermistor 8744 and/or the heated wire 8740 through the delivery circuit 8700 towards the second connector 8720. The holder 8750 can maintain a specific distance between the heated wire 8740 and the second thermistor 8744 to ensure that the gas temperature reading by the second thermistor 8744 is not influenced or made inaccurate by the temperature of the heated wire 8740. The heated wire 8740 can bend or wrap around the holder 8750 to facilitate the return of the heated wire 8740 back to the first connector 8710. The holder 8750 can couple to the tube 8730, for example by having a protrusion (i.e. a ring or partial ring), such as protrusion 9000, that inserts into at least one of the corrugations on the tube 8730 or can couple with the second connector 8720. The holder 8750 can provide a means for positioning the holder 8750 at a specific location within the tube 8730 or a certain distance from the second connector 8720. The second connector 8720 can have a port (e.g., second connector sensor port 8722) to connect the sensing conduit 8760.

Figure 14:
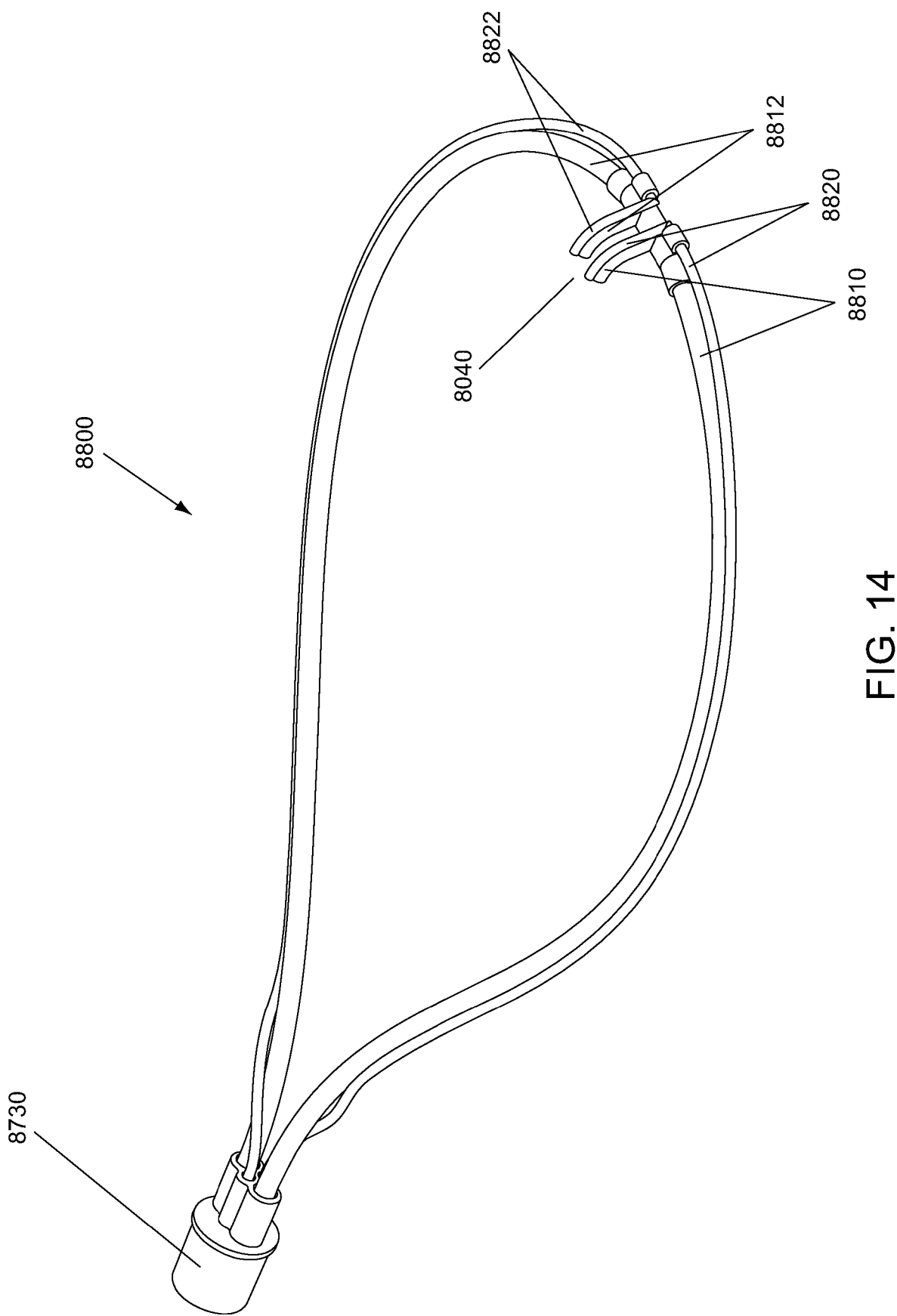
FIG. 14 illustrates the patient interface according to an embodiment of the present disclosure.

The patient interface, such as patient interface 8800, may have a nasal cannula portion 8840 that is intended to enter the nasal passages. The patient interface 8800 may have a first conduit 8810 for delivering the respiratory gas. The patient interface 8800 may have a second conduit 8820 for sensing or sampling (e.g. collecting pressure data in the nasal passages via the nasal cannula portion 8840). As shown in FIG. 14, first conduit 8810 and second conduit 8820 may extend through the nasal cannula portion 8840. In a preferred embodiment, patient interface 8800 may have two first conduits 8810, 8812 as shown in FIG. 14. In one embodiment, patient interface 8800 may have a two second conduits 8820, 8812 as shown in FIG. 14. The patient interface 8800 may mechanically and fluidly couple with the delivery circuit 8700 via a friction fit. The patient interface 8800 may have a patient fitting 8830 that may couple with the second connector 8720 to allow for the delivery of the respiratory gas through patient fitting 8830 and to a first conduit (e.g. first conduits 8810, 8812) as shown in FIG. 12. When the patient interface 8800 is coupled with the delivery circuit 8700, a seal can be created between the sensing conduit 8760 (via second connector sensor port 8722) in the delivery circuit and a patient fitting sensing conduit 8832 in the patient fitting as shown in FIG. 11. The patient fitting sensing conduit 8832 in the patient fitting pneumatically couples or communicates with a second conduit (e.g., second conduits 8820, 8822). Therefore, the second conduit can be in communication with the sensor port 8220 on the HFT device. The patient interface 8800 can be described as a sensing-enabled nasal cannula patient interface. In one embodiment shown in FIG. 11, the patient fitting sensing conduit 8832 in the patient fitting 8830 can split into two fitting sensing conduits 8834, 8836 which can pneumatically couple with two second conduits 8820, 8822. As shown in FIG. 11 and FIG. 12, first conduit 8810 may have a larger bore than the bore of second conduit 8820. The nasal cannula portion 8840 and the patient fitting 8830 can be connected by one or more patient tubes. A patient tube may be single or double lumen tube. A double lumen patient tube may have a first lumen for gas delivery and a second lumen for sensing or sampling.

The main PCB 8060 of the HFT device may have a sensor 8064 for taking measurements at or proximal the outlet of the patient interface. In one embodiment, the sensor 8064 can be a pressure sensor for measuring the airway pressure of the user. In this embodiment, the delivery circuit and the patient interface can have a conduit system that communicates with the pressure sensor. This would allow the HFT system to monitor and/or control pressure. In an alternate embodiment, the sensor 8064 can be for sampling the gas at or proximal the outlet of the patient interface. For example, the gas exhaled by the user may be sampled for $CO_2$ content. In a similar manner to the pressure sensor embodiment, the delivery circuit and the patient interface would have a conduit system that communicates with the sensor 8064 for sampling.

Different versions of delivery circuit can couple with the HFT device. As mentioned throughout, a delivery circuit can have thermal, electrical, temperature sensing, pressure sensing, and/or gas sampling capabilities and/or conduits in addition to its gas delivery function. The HFT device can be configured to recognize what type of delivery circuit is being connected to the device. For example, when a delivery circuit with gas delivery, electrical, and pressure sensing capabilities is connected, the HFT device could recognize this type of delivery circuit and consequently activate the pressure sensing aspects of the HFT device, such as pressure sensing graphics, alarms, etc. Different delivery circuits with different capabilities then could serve to activate different and various functionality of the HFT device, which may exist in the HFT device but be dormant or inactive depending on the delivery circuit connected. The HFT device may have mechanical, electrical, or optical means for recognizing the delivery circuit type connected. In one embodiment, the delivery circuit may depress certain switch on the HFT device or may contact certain electrical contacts on the HFT device. In another embodiment, the HFT device may optically read a certain delivery circuit or may scan a feature (e.g. a barcode or serial number) on a certain delivery circuit. In one example, if an operator tried to connect a delivery circuit not authorized or compatible with the HFT device (e.g. a delivery circuit connected to a sealed patient interface), the HFT device may be programmed to have limited function or not function at all. In an alternate example, if an operator tried to connect a delivery circuit connected to a sealed patient interface, the HFT device may be programmed to switch to a bi-level or Bi-PAP mode (e.g. pressure based mode) instead of an HFT mode (e.g. flow based mode) and actually allow use with a sealed mask like a CPAP, Bi-PAP, or a ventilator.

The disposable components, such as the outlet filter 8090, water chamber 8600, delivery circuit 8700, and patient interface 8800, may be individually removed from the HFT device system after use. Alternatively, groups of these disposable devices may be removed at the same time. For example, the outlet filter may be decoupled from the HFT device in one motion to disengage the water chamber, delivery circuit, and patient interface at the same time. This is advantageous to simplify the disassembly, as well as to minimize the amount of water or other contents in the disposable components that may be inadvertently leaked into the environment during disassembly.

The HFT device may further serve as a diagnostic device either during its typical HFT use or while it not being used for typical HFT treatment. The HFT device could utilize the previously mentioned sensing capabilities (e.g. pressure sensing, gas sampling, etc.) for diagnostic applications. For example, the HFT device may be used to diagnosis respiratory alignments such as sleep apnea. The HFT device could monitor, measure, record, and output the necessary information. The HFT device could incorporate functionality or accessories to include determination of stage of sleep, for example via electroencephalogram (EEG), electro-oculogram (EOG), submental electromyogram (EMG) and/or electrocardiogram/heart rate (ECG). The HFT device could incorporate functionality or accessories to include sleep parameters such as airflow, respiratory movement/effort, oxygen saturation (e.g. by oximetry), snoring, pulse rate, head movement, head position, limb movement, actigraphy, and/or peripheral arterial tone. Diagnostic accessories coupled with the HFT device could include a body sensors, pulse oximeter, a wearable wrist device, a chest or abdomen band or belt, headgear, thermistor, nasal cannula, and/or nasal/oral oral cannula, any of these which may have integrated sensors or sensing technology.

The HFT device may receive information (e.g. software upgrades) via a wired connection, USB, memory card, fiber optic, wireless connection, blue tooth, Wi-Fi, etc. The HFT device may send information (e.g. patient reports) via similar communication means. The HFT device may include wired connection such as USB port 8066 or memory card, or a wireless connection such as blue tooth or Wi-Fi.

The bulk of the work of heating the respiratory gas can be done by the heater 8052 (e.g. PTC heater element) that is part of the HFT device. This heater 8052 can be concealed by a heater plate 8050 (e.g. stainless steel material) of the HFT device, which may be in direct contact with the heat transfer plate (e.g. aluminum material) of the water chamber 8600 during use. During the heating process, the duty cycle of the heater 8052 and/or the heated wire 8740 is precisely and continuously adjusted by the HFT device's embedded software in response to feedback supplied by a temperature sensor 8054 that is located near the heater 8052 (and in some embodiments may be in contact with the heater plate 8050) and/or in response to the feedback supplied by the thermistors (e.g., first thermistor 8742, second thermistor 8744) in the delivery circuit 8700.

The HFT device may periodically decrease the gas flow rate from the set gas flow rate to allow the lungs to temporarily return to a more normal resting volume. The HFT device may automatically lower the gas flow by a certain percentage or by a certain value from the set gas flow value for a specific amount of time over a certain frequency or time period. For example, the HFT device may automatically lower the gas flow by a 20% or by 5 L/min for five seconds every ten minutes. Alternatively, the HFT device may automatically adjust the gas flow by a certain percentage, by a certain value, or a certain multiple of the expected patient tidal volume, for example based on age, weight, and/or BMI. For example, the gas flow may be decreased automatically by the HFT device to less than two times the patient expected tidal volume for five seconds every twelve breathing cycles. These types of periodic deviations from set gas flow rates could be inputted by the operator via the GUI or may be part of the programmed software. In an alternate embodiment, the HFT system may be used as a bubble CPAP system. The patient interface may have an expiratory tube connected to the nasal cannula portion for gas to exit. The distal end of the expiratory tube may be immersed in a water tank. In one embodiment, the water chamber may serve as the water tank. In an alternate embodiment, the water chamber may have a first water compartment that is fluidically coupled with the HFT device and the delivery circuit and a second water compartment that is fluidically coupled with the expiratory tube only and serves as the water tank. Water is placed in the water tank. The depth to which the expiratory tube is immersed underwater can determine the pressure generated in the airway of the patient. The gas flow may flow through the expiratory tube and bubble out into the water tank. The patient interface may be a sealed interface. The pressure sensing technology of the HFT system described throughout can be used to verify that the patient is receiving the desired pressure when the HFT system is being used as a bubble CPAP system or any embodiment described throughout. Automatic filling system technology described previously could be applied to the water tank.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

We claim:

1. A high flow therapy system for delivering heated and humidified respiratory gas to an airway of a patient, the high flow therapy system comprising:
   a non-sealing respiratory interface;
   a delivery circuit for delivering the respiratory gas to the airway of the patient via the non-sealing respiratory interface;
   a microprocessor configured to control a flow rate of the respiratory gas, wherein the microprocessor is configured to control the flow rate of the respiratory gas with a feedback loop control whereby the microprocessor is configured to control delivery of flow rates up to 60 L/min;
   a humidification chamber configured for humidifying respiratory gas delivered to the airway of the patient;
   at least one valve assembly adapted to affect the flow rate of the respiratory gas, the at least one valve assembly comprising a gas inlet, a gas outlet, a first proportional valve, and a second proportional valve, wherein the first proportional valve and the second proportional valve are coupled in parallel between the gas inlet and the gas outlet and the first proportional valve is configured to accommodate higher flow rates than the second proportional valve;
   a socket comprising a sensor port;
   at least one temperature sensor internal to the delivery circuit;
   a heated wire disposed internal to the delivery circuit to control at least one of a temperature and/or humidity of the respiratory gas; and
   a holder coupled to an internal portion of the delivery circuit, wherein the holder includes a first coupling portion and a second coupling portion, wherein the first coupling portion is configured to couple to the heated wire and the second coupling portion is configured to couple to the at least one temperature sensor such that there is a distance between the heated wire and the at least one temperature sensor, wherein the holder further includes a protrusion at a first end, the protrusion configured to insert into a corrugation of the delivery circuit,
   wherein the delivery circuit comprises a first connector, a second connector, and a sensing conduit,
   wherein the second connector connects to the non-sealing respiratory interface and the first connector comprises a first portion for connecting to a gas outlet of the humidification chamber and a second portion for mating the first connector with the socket, wherein, when the first connector is mated with the socket, the sensing conduit is configured to pneumatically connect the non-sealing respiratory interface to the sensor port; and wherein the first portion of the first connector is flexible and the second portion of the first connector is rigid.

2. The high flow therapy system of claim 1, wherein the at least one valve assembly further comprises a regulator coupled between the gas inlet and the first and second proportional valves, the regulator configured to reduce a pressure of gas received from a first source to a predetermined pressure and provide the gas to the first and second proportional valves.

3. The high flow therapy system of claim 1, wherein the at least one valve assembly comprises a flow sensor coupled between the gas outlet and the first and second proportional valves.

4. The high flow therapy system of claim 1, wherein the at least one valve assembly comprises a manifold.

5. The high flow therapy system of claim 4, wherein at least one of a regulator, the first and second proportional valves, and a flow sensor is coupled with the manifold.

6. The high flow therapy system of claim 1, wherein the delivery circuit comprises a heated delivery conduit for minimizing condensation of humidified respiratory gas.

7. The high flow therapy system of claim 6, wherein the heated wire is disposed internal to the heated delivery conduit.

8. The high flow therapy system of claim 1, further comprising a blower.

9. The high flow therapy system of claim 1, wherein the non-sealing respiratory interface is sensing-enabled.

10. The high flow therapy system of claim 1, wherein the microprocessor is configured to control at least one of a temperature of the gas, a humidity of the gas, a mixture of the gas, and a volume of gas delivered to the patient.

11. The high flow therapy system of claim 1, wherein the at least one valve assembly is configured to receive a first gas and a second gas.

12. The high flow therapy system of claim 11, wherein the at least one valve assembly has a mixing area for mixing the first gas and the second gas.

13. The high flow therapy system of claim 1, wherein the at least one temperature sensor internal to the delivery circuit is configured to provide temperature feedback to the microprocessor for controlling the heated wire.

14. The high flow therapy system of claim 1, wherein the sensing conduit is internal to the delivery circuit.

15. The high flow therapy system of claim 14, wherein the non-sealing respiratory interface comprises a nasal cannula portion and first and second conduits, the first and second conduits pneumatically coupled to the sensing conduit and to the nasal cannula portion, the nasal cannula portion configured to enter nasal passages of the patient.

16. The high flow therapy system of claim 15, wherein the non-sealing respiratory interface further comprises third and fourth conduits for providing the respiratory gas to the nasal cannula portion.

17. The high flow therapy system of claim 14, wherein the sensing conduit includes a first end for coupling with the non-sealing respiratory interface and a second end for coupling with the sensor port, wherein the second end of the sensing conduit extends through a wall of the first portion of the first connector and a wall of the second portion of the first connector such that the second end of the sensing conduit terminates at an exterior surface of the first connector.

18. The high flow therapy system of claim 1, wherein the first portion of the first connector includes an opening for receiving the gas outlet of the humidification chamber.

19. The high flow therapy system of claim 1, wherein the socket includes a slot and the second portion of the first connector is shaped to be received by the slot for engagement with the socket.

20. The high flow therapy system of claim 19, further comprising an enclosure, wherein the socket is disposed on the enclosure.

21. The high flow therapy system of claim 20, wherein the humidification chamber is removably coupled to the enclosure.

22. The high flow therapy system of claim 21, wherein the at least one valve assembly is disposed within the enclosure and the gas outlet of the at least one valve assembly is coupled with the gas inlet of the humidification chamber.

23. A high flow therapy system for delivering heated and humidified respiratory gas to an airway of a patient, the high flow therapy system comprising:

a non-sealing respiratory interface;

a delivery circuit for delivering the respiratory gas to the airway of the patient via the non-sealing respiratory interface;

a microprocessor configured to control a flow rate of the respiratory gas;

at least one temperature sensor internal to the delivery circuit;

a heated wire disposed internal to the delivery circuit to control at least one of a temperature and/or humidity of the respiratory gas; and a holder coupled to an internal portion of the delivery circuit, wherein the holder includes a first coupling portion and a second coupling portion, wherein the first coupling portion is configured to couple to the heated wire and the second coupling portion is configured to couple to the at least one temperature sensor such that there is a distance between the heated wire and the at least one temperature sensor, wherein the holder further includes a protrusion at a first end, the protrusion configured to insert into a corrugation of the delivery circuit.

* * * * *